United States Patent [19]

Stapp

[11] 3,998,848
[45] Dec. 21, 1976

[54] CYCLODIMERIZATION OF ETHYLENE OXIDE

[75] Inventor: Paul R. Stapp, Bartlesville, Okla.

[73] Assignee: Phillips Petroleum Company, Bartlesville, Okla.

[22] Filed: Oct. 3, 1975

[21] Appl. No.: 619,322

[52] U.S. Cl. .......................... 260/340.6; 260/340.9; 260/601 R
[51] Int. Cl.² ...................................... C07D 319/10
[58] Field of Search ...................... 260/340.6, 340.9

[56] References Cited

UNITED STATES PATENTS

| 3,140,296 | 7/1964 | McClure | 260/340.6 |
| 3,480,632 | 11/1969 | Scheben et al. | 260/340.6 X |

FOREIGN PATENTS OR APPLICATIONS 2,134,016  1/1973  Germany ..................... 260/340.6

*Primary Examiner*—Ethel G. Love

[57] ABSTRACT

The cyclodimerization of ethylene oxide is carried out using elemental iodine as catalyst and a sulfolane as the diluent to form 1,4-dioxane and 2-methyl-1,3-dioxolane.

5 Claims, No Drawings

CYCLODIMERIZATION OF ETHYLENE OXIDE

This invention relates to a process for cyclodimerizing ethylene oxide.

The cyclodimerizaton of ethylene oxide is well known in the art. For example, ethylene oxide can be cyclodimerized to 1,4-dioxane using acidic catalysts. The reaction can also be effected using platinum group metal catalysts such as the platinum-palladium triad catalysts. However, such systems are relatively expensive and/or produce relatively low yields of the desired cyclodimers. The present invention provides a relatively inexpensive catalyst system for cyclodimerizing ethylene oxide in good yield.

It is an object of this invention to provide a novel process for cyclodimerizing ethylene oxide.

Other objects, aspects and advantages of this invention will be readily apparent to those skilled in the art from the reading of the following disclosure.

In accordance with the present invention I have discovered that ethylene oxide can be cyclodimerized in the presence of elemental iodine and a sulfolane.

The process of the present inventon generally comprises reacting ethylene oxide in the presence of a catalytic amount of elemental iodine in a sulfolane, as hereinafter described. The sulfolane is employed as diluent in an amount ranging from about 5 to about 500 ml per 100 grams of ethylene oxide, preferably from about 25 to about 200 ml per 100 grams of ethylene oxide. The iodine is employed in approximate amounts ranging from 0.1 to 10 grams per liter of diluent, preferably about 0.5 to 5 grams of iodine per liter of diluent.

The diluent is a sulfolane having from 4 to 7 carbon atoms per molecule corresponding to the formula

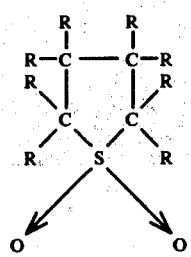

wherein each R is individually selected from the group consisting of hydrogen and alkyl having from 1 to 3 carbon atoms.

Examples of the diluents which can be employed in the practice of the present invention include: tetrahydrothiophene-1,1-dioxide, also known as sulfolane, and the substituted sulfolanes such as 2-methyl sulfolane, 3-methyl sulfolane, 2-ethyl sulfolane, 3-ethyl sulfolane, 2-propyl sulfolane, 3-propyl sulfolane, 2-isopropyl sulfolane, 3-isopropyl sulfolane, 2,2-dimethyl sulfolane, 2,3-dimethyl sulfolane, 2,4-dimethyl sulfolane, 2,5-dimethyl sulfolane, 3,3-dimethyl sulfolane, 3,4-dimethyl sulfolane, 2,3,4-trimethyl sulfolane, 2,3,5-trimethyl sulfolane, 2-methyl-3-ethyl sulfolane, and the like and mixtures thereof. Presently preferred diluents include unsubstituted sulfolane, 2-methyl sulfolane and 3-methyl sulfolane. The more presently preferred diluent is unsubstituted sulfolane.

The process of this invention is carried out at a temperature in the approximate range of 75° to 300° C, preferably in the approximate range of 150° to 250° C.

The process is carried out for a time sufficient to effect the desired degree of conversion of the ethylene oxide. The reaction time will depend upon the temperature of reaction and the concentration of the catalyst in the reaction mixture to effect the desired conversion.

The process of this invention is carried out at any convenient pressure. Autogenous pressure is usually employed.

Following completion of the reaction period, the reaction mixture can be separated by any convenient method, such as by fractional distillation. In a batch process, the catalyst system, i.e., iodine in sulfolane remains in the distillation kettle residue and can be used again for the cyclodimerization of a fresh charge of ethylene oxide.

The process of this invention can also be carried out in a continuous manner by passing a mixture of ethylene oxide, iodine and a sulfolane through a suitable reaction zone under suitable conditions of temperature and residence time to provide the desired cyclodimerization. The effluent from such a reaction zone can be fractionally distilled and the catalyst system recycled to the reaction zone.

The cyclodimerization products of the process of this invention are 1,4-dioxane and 2-methyl-1,3-dioxolane. The relative proportions of these dimers can be varied by proper selection of reaction conditions to give a preponderance of one isomer over the other or substantially equal amounts of each dimer, if desired.

The cyclodimers produced in accordance with the present invention are well known in the art. They are useful as solvents in a variety of applications. They can also be used as monomers in the formation of high molecular weight polymers.

The following examples illustrate the invention.

EXAMPLE I

A one liter autoclave equipped with stirrer was charged with 200 ml of distilled tetrahydrothiophene-1,1-dioxide, 0.5 grams of iodine crystals, and 159 grams (3.614 moles) of ethylene oxide. The mixture was heated for 6 hours at 225° C while the pressure decreased from 650 to 200 psig. The autoclave reactor was vented and the reaction mixture transferred, using ether to wash the reactor, to a distilling flask. The reaction mixture was then fractionally distilled at atmospheric pressure to recover three fractions as shown below:

| Fraction No. | Boiling Range, ° C | Weight, Grams |
|---|---|---|
| 1 | 25–83 | 57.9 |
| 2 | 83–98 | 92.8 |
| 3 | 98–102 | 10.6 |

The above described fractions were analyzed by gas-liquid chromatography with the results shown in the following table.

| Fraction No. | Acetaldehyde, Grams | 2-Methyl-1,3-dioxolane, Grams | 1,4-Dioxane Grams |
|---|---|---|---|
| 1 | 15.07 | 6.55 | 2.77 |
| 2 | 2.37 | 25.60 | 63.70 |
| 3 | 1.17 | 1.34 | 7.51 |
| Total | 18.61 | 43.49 | 73.98 |

The above results show that the percent yield of 2methyl-1,3-dioxolane was 27.4 and 1,4-dioxane was 46.5 based on the starting ethylene oxide. The above results show that good yields of the cyclodimers of the ethylene oxide were obtained according to the process of the instant invention.

EXAMPLE II

For comparison, a run was conducted using benzene in place of the tetrahydrothiophene-1,1-dioxide employed in Example I.

The one liter autoclave utilized in Example I was charged with 200 ml of benzene, 0.5 grams of iodine crystals, and 161 grams (3.659 moles) of ethylene oxide and was heated for six hours at 225° C while the pressure decreased from 825 to 800 psig. The reactor was then vented and the product transferred to a sample bottle. The recovered reaction mixture weighed 358.7 grams. The reaction mixture was analyzed by gas-liquid chromatograhy and showed by the analysis the presence of only ethylene oxide and benzene although a trace of acetaldehyde may have been present. No 1,4-dioxane or 2-methyl-1,3-dioxolane was detected in the mixture. The results of this run demonstrate that iodine in benzene under the conditions employed was not effective for the cyclodimerization of ethylene oxide.

EXAMPLE III

For further comparison a run was conducted following the general procedure of Example I, but without the iodine catalyst.

The one liter autoclave reactor utilized in the above described runs was charged with 200 ml of distilled tetrahydrothiophene-1,1-dioxide and 160 grams (3.636 moles) of ethylene oxide. The reaction mixture was heated for 6 hours at 225° C while the pressure decreased from 700 to 525 psig. The reactor was vented and the reaction mixture transferred to a distillation flask and the ethylene oxide removed by distillation at atmospheric pressure. Only ethylene oxide was found in the distillate obtained at room temperature. The residue was then distilled further to give 196 ml of tetrahydrothiophene-1,1-dioxide with a boiling range of 148°–152° C at 10 millimeters Hg pressure. No cyclodimers of ethylene oxide were observed in the reaction mixture obtained according to the conditions described above. The results of this run indicate that tetrahydrothiophene-1,1-dioxide alone was not a suitable catalyst for the cyclodimerization of ethylene oxide under the conditions employed.

Reasonable variations and modifications, which will be apparent to those skilled in the art, can be made in this invention without departing from the spirit and scope thereof.

What is claimed is:

1. A process for the cyclodimerizaton of ethylene oxide which comprises reacting ethylene oxide in the presence of a catalytic amount of a catalyst system consisting of elemental iodine in a sulfolane having from 4 to 7 carbon atoms per molecule corresponding to the formula

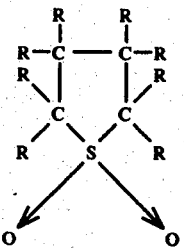

wherein each R is individually selected from the group consisting of hydrogen and alkyl having from 1 to 3 carbon atoms.

2. The process of claim 1 wherein said reaction is carried out at a temperature in the approximate range of 75° to 300° C.

3. The process of claim 1 wherein the amount of said sulfolane is in the approximate range of 5 to 500 ml per 100 g. of said ethylene oxide.

4. The process of claim 1 wherein the amount of said iodine is in the approximate range of 0.1 to 10 grams per liter of said sulfolane.

5. The process of claim 1 wherein said sulfolane is tetrahydrothiophene-1,1-dioxide.

* * * * *